United States Patent [19]

Modi

[11] Patent Number: 6,083,492

[45] Date of Patent: Jul. 4, 2000

[54] HYDROPHOBICALLY MODIFIED POLYSACCHARIDE IN ANHYDROUS ANTIPERSPIRANT PRODUCTS

[75] Inventor: Jashawant J. Modi, Hockessin, Del.

[73] Assignee: Hercules Incorporated, Wilmington, Del.

[21] Appl. No.: 09/224,106

[22] Filed: Dec. 17, 1998

[51] Int. Cl.⁷ .............. A61K 7/32; A61K 7/00; A61K 31/74
[52] U.S. Cl. .............. 424/65; 424/66; 424/67; 424/68; 424/400; 424/401; 424/78.02
[58] Field of Search ................ 424/65, 66, 67, 424/68, 400, 401, 78.02, DIG. 5

[56] References Cited

U.S. PATENT DOCUMENTS

| | | | |
|---|---|---|---|
| 5,158,772 | 10/1992 | Davis et al. | 424/401 |
| 5,609,855 | 3/1997 | Oh et al. | 424/66 |
| 5,744,130 | 4/1998 | Guskey et al. | 424/66 |

*Primary Examiner*—Shelley A. Dodson
*Attorney, Agent, or Firm*—David Edwards

[57] ABSTRACT

A solid stick, underarm product composition is composed of a liquid vehicle, an antiperspirant salt, a dibenzylidene alditol gelling agent, and a co-gelling agent of a hydrophobically modified water soluble polysaccharide polymer which comprises a water soluble polysaccharide polymer backbone, a hydrophobic moiety of $C_8$–$C_{24}$ alkyl, aryl alkyl, alkyl aryl groups and mixtures thereof, wherein the hydrophobic moiety is present in an amount up to the amount which renders said polysaccharide less than 1% by weight soluble in water, and dibenzylidene alditol, antiperspirant active and a liquid vehicle. This underarm product can be either clear or hazy.

31 Claims, No Drawings

HYDROPHOBICALLY MODIFIED POLYSACCHARIDE IN ANHYDROUS ANTIPERSPIRANT PRODUCTS

This invention relates to the use of hydrophobically modified polysaccharides in underarm stick products such as antiperspirant/deodorant products.

BACKGROUND OF THE INVENTION

Prior to the present invention, nonionic water-soluble cellulose ethers have been used in clear underarm stick products. Gel antiperspirant/deodorant sticks typically include a liquid vehicle, an antiperspirant salt and/or deodorant agent, a gelling agent, and one or more emollients. Clear gel antiperspirant or deodorant sticks are more desirable than opaque sticks for cosmetic reasons. For clear sticks, the gelling agents of choice are dibenzylidene alditols, e.g., dibenzylidene sorbitol (DBS), also known as dibenzylidene monosorbitol acetal (DBMSA), because they are able to form strong free standing gels that are clear, are relatively stable, and have relatively good shelf life although they tend to degrade in certain environments. The degradation of the DBS is because of the presence of acidic antiperspirant salt in the stick. Commercially available DBS gel antiperspirant sticks generally contain more than 2% DBS in order to have sufficient hardness. However, such sticks do not have optimum clarity or stability.

Widely used commercially available nonionic water soluble cellulose ethers that are used in antiperspirant/deodorant sticks as co-gelling agents are, for example, methyl cellulose (MC), hydroxypropylmethylcellulose (HPMC), hydroxyethylcellulose (HEC), and hydroxypropylcellulose (HPC); HPC is preferred for clear antiperspirant/deodorant sticks. The use of these prior art cellulose ethers in antiperspirant/deodorant stick products sometimes have processing difficulties such as compatibility with other ingredients, solubility with certain other ingredients, clarity (when needed), and stability under alkaline conditions of the products.

International Publication Number WO 96/26709 and U.S. Pat. Nos. 5,705,171 and 5,725,846 disclose use of hydroxyalkylcellulose and specifically hydroxypropylcellulose in a clear anhydrous antiperspirant stick. U.S. Pat. No. 5,534,245 discloses use of a water-soluble cellulose polymer in a water containing roll-on or soft gel-like antiperspirant.

The stick form can be distinguished from a gel or a paste in that in a stick, the formulated product can maintain its shape for extended period of time outside the package except for the shrinkage due to solvent evaporation. U.S. Pat. No. 5,725,846, 5,705,171, 4,720,381, and 4,725,430 disclose use of hydroxypropylcellulose in a transparent anhydrous antiperspirant stick composition. U.S. Pat. No. 4,383,988 discloses use of hydroxypropylcellulose acetate in water containing pourable antiperspirant gel composition. EP Patent Application 0260030 discloses the use of chemically modified cellulose, such as hydroxypropylcellulose, hydroxyethylcellulose, and methylcellulose in water containing clear deodorant sticks. However, none of the prior art discloses the use of hydrophobically modified polysaccharides in a transparent anhydrous antiperspirant stick.

SUMMARY OF THE INVENTION

The present invention is directed to a solid stick antiperspirant/deodorant composition comprising (a) a liquid vehicle, (b) an antiperspirant salt, (c) dibenzylidene alditol gelling agent, and (d) a co-gelling agent of a hydrophobically modified water soluble polysaccharide polymer where the hydrophobic moiety is selected from the class consisting of $C_8$–$C_{24}$ alkyl, aryl alkyl, alkyl aryl groups and mixtures thereof, wherein the hydrophobic moiety is present in an amount up to the amount which renders said polysaccharide less than 1% by weight soluble in water.

DETAILED DESCRIPTION OF THE INVENTION

It has been found that hydrophobically modified water soluble non-ionic polysaccharide polymer can be used as a co-gelling agent for certain solid stick, antiperspirant compositions that use dibenzylidene alditols as the gelling agent to produce either comparable or superior products that are currently being marketed commercially.

Any water-soluble non-ionic polysaccharide can be used as the backbone to form the hydrophobically modified polysaccharide of this invention. Examples of water soluble non-ionic polysaccharides are cellulose ethers, guar and guar derivatives (e.g., hydroxyethyl guar or hydroxypropyl guar), and starch and starch derivatives (e.g., hydroxyethyl starch or hydroxypropyl starch).

A preferred backbone is cellulose ethers. Thus, e.g., hydroxyethylcellulose (HEC), hydroxypropylcellulose (HPC), methylcellulose (MC), hydroxypropylmethylcellulose (HPMC), ethylhydroxyethylcellulose (EHEC), methylhydroxyethylcellulose (MHEC) and their nonionic derivatives can all be as the backbone for the modification. The polysaccharide of this invention has to be water-soluble unmodified or has a sufficient degree of nonionic substitution to cause them to be water-soluble and a hydrophobic moiety of $C_8$–$C_{24}$ alkyl, aryl alkyl, alkyl aryl groups and mixtures thereof. The hydrophobic moiety is present in an amount up to the amount that renders said polysaccharide less than 1% by weight soluble in water. When the hydrophobe is an alkyl, aryl alkyl, or alkyl aryl moiety, the number of carbon atoms has an upper limit of 24, preferably 22, more preferably 18, and most preferably 16. The lower limit of the carbon atoms of the hydrophobic moiety is 8 and preferably 12.

The preferred polysaccharide backbone is hydroxyethylcellulose (HEC) and hydropropylcellulose (HPC). The HEC that is modified to function in this invention is a commercially available material, that is marketed by the Aqualon Company, a division of Hercules Incorporated, Wilmington, Del. U.S.A., under the trademarks Natrosol® Plus and Polysurf®.

The alkyl modifier group can be attached to the polysaccharide backbone via an ether, ester, or urethane linkage. Ether is the preferred linkage as the reagents most commonly used to effect etherification because it is readily obtainable; the reaction is similar to that commonly used for the initial etherification, and the reagents used in the reaction are usually more easily handled than the reagents used for modification via the other linkages. The resulting linkage is also usually more resistant to further reactions.

The hydrophobic moiety is generally contained in an amount of about 0.05 to about 10 wt. %, preferably about 0.1 to about 5 wt. based on the dry weight of the substituted polymer. Examples of modifying radicals are 2-ethylhexyl, octyl, cetyl, and octadecyl.

Gelling Agent

Another essential ingredient of the present invention is the gelling agent dibenzylidene alditols such as dibenzylidene sorbitol (DBS) which is also known as dibenzylidene monosorbitol acetal (DBMSA), dibenzylidene xylitol, and dibenzylidene ribitol. The benzylidene group may be unsubstituted or substituted.

Liquid Vehicle

Another essential ingredient of the present invention is a liquid vehicle such as polyhydric alcohol having from 3 to 6 carbon atoms and 2 to 6 hydroxyl groups such as diethylene glycols, triethylene glycol, 1,2-propylene glycol, 1,3-propylene glycol, dipropyleneglycol, tripropylene glycol, 2-methyl-1,3-propendiol, butelene glycol, sorbitol, 2,4-dihydroxy-2-methylpentane, and the like, and mixtures thereof. The liquid vehicle may contain ethanol, isopropanol, or ethylene glycol.

Antiperspirant Agent

Another essential ingredient of the formulation is antiperspirant salts that have significant antiperspirant activity when applied to human skin. The salts may be inorganic or organic. It includes any of the conventional aluminum, zirconium, zinc and their combination known to be useful in antiperspirant compositions. These salts include aluminum halides, aluminum hydroxy halides, and mixtures or complexes thereof with zirconyl oxyhalides and zirconyl hydroxyhalides. It is preferred to use polyhydric alcohol solution of the antiperspirant salts. The solubilized form of some of the antiperspirant salts are commercially available such as Westchlor® A2Z 8106 from Westwood Chemical Corporation of Middletown, N.Y.

Chelating Agent

Another ingredient that may be in the system is a chelating agent. Examples of chelating agents are salts of ethylenediamine tetraacetic acid (EDTA) such as tetra sodium ethylenediaminetetraacetate, ethanoldigl disodium salt (EDG), etc. The chelating agent may helps in improving color, clarity and as stabilizer for the gelling agent DBS.

Emollient

Another ingredient that may be present in the system is an emollient such as fatty acid esters, e.g., isopropyl palmitate; diesters of adipic, phthalic, and sebasic acids; propylene glycol diesters of short chain fatty acids, nonvolatile silicone oils, volatile silicone oils; silicone elastomers, $C_{12}$–$C_{15}$ alkyl benzoate; fatty alcohol such as stearyl alcohol; alkyl ether derivatives of polyethylene glycols, polypropylene glycols, and other emollients that are conventionally used in the personal care and cosmetic industry to enhance application properties of the sticks. An emollient can be used alone or in combination with other emollients in the present invention.

Stabilizer

Another ingredient that may be present in the system is a stabilizer for dibenzylidene alditols such as sodium or potassium hydroxide; zinc compounds such as acetate, oxide, carbonate; di or triethanolamine; sodium benzoate or octanoate; urea; disodium succinate.

Other Ingredients

Other ingredients that may be present in the system are fragrances, humectants, gel hardeners, fillers, colorants, preservatives, bactericides, UV absorbers, antioxidants, emulsifiers, activity enhancers, sunscreen, oils, and monohydric alcohols such as ethanol.

In accordance with the present invention, the underarm composition has by weight percent of about 70% to 95% liquid vehicle, about 0.5% to 20% antiperspirant salt, 0.3% to 5.0% dibenzylidene alditol, and 0.1 to 3.0% hydrophobically modified water soluble polysaccharide.

The following examples are merely set forth for illustrative purposes, but it to be understood that other modifications of the present invention within the skill of artisans in the industry can be made without departing from the spirit and scope of the invention.

EXAMPLES

In the following Examples, hydrophobically modified hydroxyalkyl-cellulose of HMHAC 1, HMHAC 2, Natrosol® Plus 430, and Polysurf® 67 products and were evaluated and compared with hydroxyalkylcellulose (HAC) such as Klucel® product in an antiperspirant (AP) formulation of the prior art.

(A) Sample Preparation:

Examples 1 to 9 were prepared using two phase process (two step process). Example 10 was prepared using single phase (one step process). Briefly, in two phases, Gelling agents and the antiperspirant active ingredient were heated in separate vessels and then mixed together. In a single phase all ingredients of the formulation were mixed in a same container. More detail procedure for each example is attached.

(B) Samples Evaluations:

Table 1 provides comparative data for various HMHAC of this invention and for HAC (Klucel®). The samples were evaluated for:

Gel Strength

Clarity

Color

Syneresis

Each formulation was stored at room temperature (about 25° C.), 40° C., and at 5° C. for at least one week and brought to about 25° C. temperature prior to evaluating for the above characteristics.

Gel Strength: The gel strength was measured in grams using Voland-Stevens LFRA Texture Analyzer Unit with 0.5 inch (1.11 mm) diameter probe. The probe was lowered 2 mm into the gel at a speed of 2 mm/second. Three measurements were taken and the average of the three measurements was reported.

Clarity: Five subcategories were assigned to differentiate clarity differences between various samples. These were: Clear, Slightly Hazy, Hazy, Translucent, and Opaque.

Clear: Antiperspirant samples free from any material that dims, obscures, or darkens or prevents one from seeing an object located on the other side of it. For example, the 1/16" size print on a paper located behind the sample is easily and clearly readable.

Slightly Hazy: Antiperspirant samples through which 1/16" print is still readable but the print is not as sharp as with the "Clear" sample.

Hazy: Antiperspirant samples through which object located behind the sample can be still viewed and identified but are not as sharp as for the slightly hazy sample. The 1/16" prints are readable with some difficulty.

Translucent: Antiperspirant samples through which light is transmitted and an object can be identified but the image is fuzzy and not distinct. The 1/16" prints are not readable.

Opaque: The 1/16" print when located behind the sample cannot be seen or identified.

Color: Five subcategories were also assigned to differentiate clarity differences between various samples. These were water white, Light Yellow, Yellow, Dark Yellow, and Amber.

The colors and clarity were determined by a two person panel who are familiar with testing or rating samples; this panel rated the samples visually as compared to each other for clarity and color under ambient room light. In order to insure consistency in the rating, all samples were rated at the same time under the same conditions.

Syneresis: It is the weeping out of liquid from the sample after standing for a period of time.

EXAMPLE A

Formulation:

|  | Percent |
|---|---|
| Phase 1: | |
| Propylene glycol | 34.93 |
| Millithix ® 925 | 4.33 |
| Subtotal | 39.26 |
| Phase 2: | |
| Propylene glycol | 20.60 |
| Tetrasodium EDTA | 0.22 |
| Westchlor ® A2Z8106 | 39.65 |
| Abil ® B8851 | 0.27 |
| Subtotal | 60.74 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol in the beaker was heated to about 125–130° C. while stirring at the minimum speed of about 50 rpm with a Caframo Model RZR1 electric mixer equipped with a Jiffy Model HS150 2.62 inch diameter mixer. The mixer speed was increased to about 150–200 rpm and the Millithix material was added at a temperature of about 120° C. and mixed for 60 minutes until dissolved.

Phase 2.

Approximately one-third of the total propylene glycol was charged to a 600 ml beaker and immersed in a circulating water bath. The propylene glycol in the beaker was heated to about 80–85° C. while stirring at minimum speed (~50 rpm) with a Caframo Model RZR1 electric mixer equipped with a single two-inch diameter propeller blade. The EDTA was added at a temperature of about 80–85° C. and mixed well to disperse. The mixer speed was increased to about 150–200 rpm and the Westchlor material was added at 82° C. while mixing and mixed for five minutes. The Abil material was then added at 80° C. while mixing and mixed for five minutes.

Combined Phases:

Phase 2, at 82° C., was added to Phase 1 at 1 32° C. while mixing and mixed for five minutes at reduced speed to avoid air entrainment. The combined solution was re-heated to 125° C., then poured into four four-ounce jars and four 17-ml vials for testing and allowed to cool to room temperature.

Source and Description of Products Used

EXAMPLE A

Source and Description of Products Used

| Propylene glycol | | EM Industries, Inc. Gibbstown, NJ |
|---|---|---|
| Millithix 925 | Dibenzylidene sorbitol | Milliken Chemicals Spartanburg, SC |
| Tetrasodium EDTA | | J. T. Baker co. Phillipsberg, NJ |
| Westchlor A2Z 8106 | Al/Zr Penta-chlorohydrex-gly | Westwood Chemical Corp. Middletown, NY |
| Abil B8851 | Dimethicone copolymer | Goldschmidt Chemical Corp. Hopewell, VA |

*HMHAC1 is hydrophobically modified hydroxyethylcellulose that contains a long chain ($C_{16}$) alkyl group and has Brookfield viscosity of 25 cps at about 1.0% at 25° C.

EXAMPLE B

Formulation:

|  | Percent |
|---|---|
| Phase 1: | |
| Propylene glycol | 36.10 |
| HMHAC1* | 1.12 |
| Subtotal | 37.22 |
| Phase 2: | |
| Propylene glycol | 21.30 |
| Tetrasodium EDTA | 0.22 |
| Westchlor A2Z8106 | 40.98 |
| Abil B8851 | 0.28 |
| Subtotal | 62.78 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol in the beaker was heated to about 120–125° C. while stirring at the minimum speed of ~50 rpm with a Caframo Model RZR1 electric mixer equipped with a Jiffy Model HS150 2,62 inch diameter mixer. The HMHAC1 was added at about 75–80° C. while mixing and the mixture was continued heating to about 125–130° C.

Phase 2.

Approximately one-third of the total propylene glycol was charged to a 600 ml beaker and immersed in a circulating water bath. The propylene glycol in the beaker was heated to about 80–85° C. while stirring at minimum speed (~50 rpm) with a Caframo Model RZR1 electric mixer equipped with a single two-inch diameter propellor blade. The EDTA was added at about 60–65° C. and mixed well to disperse. The mixer speed was increased to about 150–200 rpm and the Westchlor material was added at about 82° C. while mixing and mixed for five minutes. The Abil material was then added at about 75–80° C. while mixing and mixed for five minutes.

Combined Phases:

Phase 2, at about 81° C., was added to Phase 1 at about 126° C. while mixing and mixed for five minutes at reduced speed to avoid air entrainment. The combined solution was re-heated to about 120° C., then poured into four four-ounce jars and four 17-ml vials for testing and allowed to cool to room temperature.

EXAMPLE 1

Formulation:

| | Percent |
|---|---|
| Phase 1: | |
| Propylene glycol | 34.55 |
| HMHAC1 | 1.07 |
| Millithix 925 | 4.29 |
| Subtotal | 39.91 |
| Phase 2: | |
| Propylene glycol | 20.38 |
| Tetrasodium EDTA | 0.21 |
| Westchlor A2Z8106 | 39.22 |
| Abil B8851 | 0.27 |
| Subtotal | 60.09 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 120–125° C. while stirring at the minimum speed of ~50 rpm with a Caframo Model RZR1 electric mixer equipped with a Jiffy Model HS150 2.62 inch diameter mixer. The HMHAC1 was added at about 75–80° C. while mixing and the mixture was continued to be heated to about 105–110° C. The mixer speed was increased to about 150–200 rpm and the Millithix material was added at about 120° C. and mixed for 90 minutes until dissolved.

Phase 2.

Approximately one-third of the total propylene glycol was charged to a 600 ml beaker and immersed in a circulating water bath. The propylene glycol in the beaker was heated to about 80–85° C. while stirring at minimum speed (~50 rpm) with a Caframo Model RZR1 electric mixer equipped with a single two-inch diameter propellor blade. The EDTA was added at about 80–85° C. and mixed well to disperse. The mixer speed was increased to 150–200 rpm and the Westchlor material was added while mixing and mixed for five minutes. The Abil product then was added at about 75–80° C. while mixing and mixed for five minutes.

Combined Phases:

When the Millithix material was all dissolved, Phase 2, at about 81° C., was added to Phase 1 at about 130° C. while mixing and mixed for five minutes at reduced speed to avoid air entrainment. The combined solution was re-heated to about 120° C., then poured into four four-ounce jars and four 17-ml vials for testing and allowed to cool to room temperature.

EXAMPLE C

Formulation:

| | Percent |
|---|---|
| Phase 1: | |
| Propylene glycol | 36.18 |
| Klucel ® MFF* | 0.34 |
| Millithix 925 | 0.56 |
| Subtotal | 37.08 |
| Phase 2: | |
| Propylene glycol | 21.34 |
| Tetrasodium EDTA | 0.22 |
| Westchlor A2Z8106 | 41.07 |
| Abil B8851 | 0.28 |
| Subtotal | 62.92 |
| Total | 100.00 |

*Klucel MFF is the trademark that covers hydroxypropylcellulose that is nonionic and has a Brookfield viscosity of 4,000 to 6,500 at 2.0% at 25° C.

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol in the beaker was heated to about 85–90° C. while stirring at ~450–500 rpm with a Caframo Model RZR1 electric mixer equipped with a single two-inch diameter propellor blade. The Klucel MFF polymer was added at about 85–90° C. while mixing and the mixture was continued heating to about 105–110° C. The Millithix material was then added and mixed for about 40 minutes until dissolved.

Phase 2.

Approximately one-third of the total propylene glycol was charged to a 600 ml beaker and immersed in a circulating water bath. The propylene glycol in the beaker was heated to about 65–70° C. while stirring at ~450–500 rpm with a Caframo Model RZR1 electric mixer equipped with a single 1½" diameter propellor blade. The EDTA was added at about 65–70° C. and mixed well to disperse. The Westchlor material was added while mixing and mixed for five minutes. The Abil material was then added while mixing and mixed for five minutes.

Combined Phases:

When the Millithix material was all dissolved, Phase 1 was cooled to about 95–100° C. Phase 2 was then added to Phase 1 while mixing and mixed for five minutes at minimum speed to avoid air entrainment. The combined solution at about 80–85° C. was then poured into four four-ounce jars and four 17-ml vials for testing and allowed to cool to room temperature.

EXAMPLE 2

Formulation:

| | Percent |
|---|---|
| Phase 1: | |
| Propylene glycol | 36.18 |
| Natrosol ®Plus 430* | 0.34 |
| Millithix 925 | 0.56 |
| Subtotal | 37.08 |
| Phase 2: | |
| Propylene glycol | 21.34 |
| Tetrasodium EDTA | 0.22 |
| Westchlor A2Z8106 | 41.07 |

EXAMPLE 2-continued

Formulation:

| | Percent |
|---|---|
| Abil B8851 | 0.28 |
| Subtotal | 62.92 |
| Total | 100.00 |

Natrosol ® Plus 430 is the trademark that covers nonionic hydrophobically modified hydroxyethylcellulose. It has long chain ($C_{16}$) alkyl group and an aqueous, Brookfield viscosity at 1.0% of between 5000–9000 cps at spindle 3, 6 rpm.

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 70–75° C. while stirring at a minimum speed of ~50 rpm with a Caframo Model RZR1 electric mixer equipped with a Jiffy Model HS150 2.62 inch diameter mixer. The Natrosol®Plus 430 product was added at about 70–75° C. while mixing and the mixture was continued heating to about 105–110° C. The mixer speed was increased to about 150–200 rpm and the Millithix material was added at about 105–110° C. and mixed for 40 minutes until dissolved.

Phase 2.

Approximately one-third of the total propylene glycol was charged to a 600 ml beaker and immersed in a circulating water bath. The propylene glycol in the beaker was heated while stirring at minimum speed (~50 rpm) with a Caframo Model RZR1 electric mixer equipped with a single two-inch diameter propellor blade. The mixer speed was increased to about 150–200 rpm and the EDTA was added at about 60–65° C. and mixed well to disperse. The Westchlor material was added while mixing and mixed for five minutes. The Abil material then was added while mixing and mixed for five minutes.

Combined Phases:

When the Millithix material was all dissolved, Phase 1 was cooled to about 105–110° C. Phase 2 was then added to Phase 1 while mixing and mixed for five minutes at reduced speed to avoid air entrainment. The combined solution at about 95–100° C. was then poured into four four-ounce jars and four 17-ml vials for testing and allowed to cool to room temperature.

EXAMPLE 3

Formulation:

| | Percent |
|---|---|
| Phase 1: | |
| Propylene glycol | 36.18 |
| Polysurf 67* | 0.34 |
| Millithix 925 | 0.56 |
| Subtotal | 37.08 |
| Phase 2: | |
| Propylene glycol | 21.34 |
| Tetrasodium EDTA | 0.22 |

EXAMPLE 3-continued

Formulation:

| | Percent |
|---|---|
| Westchlor A2Z8106 | 41.07 |
| Abil B8851 | 0.28 |
| Subtotal | 62.92 |
| Total | 100.00 |

*Polysurf 67 is a trademark that covers nonionic hydrophobically modified hydroxyethylcellulose. It has long chain ($C_{16}$) alkyl group and an aqueous Brookfield viscosity at 1.0% of between 6000–13000 cps, at spindle 3, 6 rpm.

Procedure:

Phase 1.

Approximately two-thirds of the total propylene glycol was charged to a one-liter beaker and immersed in a circulating oil bath. The beaker paper was kept covered with saran wrap throughout the preparation to minimize loss of volatiles. The propylene glycol was heated while stirring at the minimum speed of ~50 rpm with a Caframo Model RZR1 electric mixer equipped with a Jiffy Model HS150 2.62 inch diameter mixer. The Polysurf 67 material was added at 60–65° C. while mixing and the mixture was continued to heat to about 110–115° C. The mixer speed was increased to about 150–200 rpm and the Millithix material was added and mixed for about 20 minutes until dissolved.

Phase 2.

Approximately one-third of the total propylene glycol was charged to about 600 ml beaker and immersed in a circulating water bath. The propylene glycol was heated in a beaker while stirring at minimum speed (~50 rpm) with a Caframo Model RZR1 electric mixer equipped with a single two-inch to diameter propellor blade. The EDTA was added at about 65–70° C. and mixed well to disperse. The mixer speed was increased to 150–200 rpm and the Westchlor material was added while mixing and mixed for five minutes. The Abil material then was added while mixing and mixed for five minutes.

Combined Phases:

When the Millithix material was all dissolved, Phase 1 was cooled to about 105–110° C. Phase 2 was then added to Phase 1 while mixing and mixed for five minutes at reduced speed to avoid air entrainment. The combined solution at about 85–90° C. was then poured into four four-ounce jars and four 17-ml vials for testing and allowed to cool to room temperature.

EXAMPLE D

Formulation:

| | Percent |
|---|---|
| Phase 1: | |
| Propylene glycol | 35.90 |
| Klucel MFF | 0.56 |
| Millithix 925 | 1.11 |
| Subtotal | 37.57 |
| Phase 2: | |
| Propylene glycol | 21.18 |
| Westchlor A2Z8106 | 0.22 |
| Tetrasodium EDTA | 40.75 |

EXAMPLE D-continued

Formulation:

|  | Percent |
|---|---|
| Abil B8851 | 0.28 |
| Subtotal | 62.43 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 125–130° C. while stirring at the minimum speed of ~50 rpm with a Caframo Model RZR1 electric mixer equipped with a Jiffy Model HS150 2.62 inch diameter mixer. The Klucel MFF material was added at about 60–65° C., and the mixture was continued heating to about 120–130° C. The mixer speed was increased to 150–200 rpm and the Millithix material was added at about 120° C. and mixed for about 40 minutes to dissolve.

Phase 2.

Approximately one-third of the total propylene glycol was charged to about 600 ml beaker and immersed in a circulating water bath. The propylene glycol was heated in a beaker to about 80–85° C. while stirring at minimum speed (~50 rpm) with a Caframo Model RZR1 electric mixer equipped with a single two-inch diameter propellor blade. The EDTA was added at about 75–80° C. and mixed well to disperse. The mixer speed was increased to 150–200 rpm and the Westchlor was added at about 80–85° C. while mixing and mixed. The Abil was then added at about 70–75° C. while mixing and mixed for about 20 minutes.

Combined Phases:

Phase 2, at about 82° C., was added to Phase 1 at about 131° C. while mixing and mixed for about 10 minutes at reduced speed to avoid air entrainment. The combined solution was re-heated to about 120–125° C. while mixing, then poured into four four-ounce jars and four 17-ml vials for testing and allowed to cool to room temperature.

EXAMPLE 4

Formulation:

|  | Percent |
|---|---|
| Phase 1: |  |
| Propylene glycol | 35.90 |
| HMHAC2* | 0.56 |
| Millithix 925 | 1.11 |
| Subtotal | 37.57 |
| Phase 2: |  |
| Propylene glycol | 21.18 |
| Tetrasodium EDTA | 0.22 |
| Westchlor A2Z8106 | 40.75 |
| Abil B8851 | 0.28 |
| Subtotal | 62.43 |
| Total | 100.00 |

*HMHAC2 is a nonionic (C8) alkylated hydroxypropylcellulose polymer.

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 125–130° C. while stirring at the minimum speed of ~50 rpm with a Caframo Model RZR1 electric mixer equipped with a Jiffy Model HS150 2.62 inch diameter mixer. The HMHAC2 was added at about 75–80° C., and the mixture was continued heating to about 120–130° C. The mixer speed was increased to about 150–200 rpm and the Millithix material was added at about 120° C. and mixed for 30 minutes to dissolve.

Phase 2.

Approximately one-third of the total propylene glycol was charged to about 600 ml beaker and immersed in a circulating water bath. The propylene glycol was heated in a beaker to about 80–85° C. while stirring at minimum speed (~50 rpm) with a Caframo Model RZR1 electric mixer equipped with a single two-inch diameter propellor blade. The EDTA was added at about 75–80° C. and mixed well to disperse. The mixer speed was increased to about 150–200 rpm and the Westchlor material was added at about 80–85° C. while mixing and mixed. The Abil material was then added at about 80–85° C. while mixing and mixed for ten minutes.

Combined Phases:

Phase 2, at about 82° C., was added to Phase 1 at about 131° C. while mixing and mixed for about 10 minutes at reduced speed to avoid air entrainment. The combined solution was re-heated to about 120–125° C. while mixing, then poured into four four-ounce jars and four 17-ml vials for testing and allowed to cool to room temperature.

EXAMPLE 5

Formulation:

|  | Percent |
|---|---|
| Phase 1: |  |
| Propylene glycol | 35.90 |
| Natrosol ® Plus 430 | 0.56 |
| Millithix 925 | 1.11 |
| Subtotal | 37.57 |
| Phase 2: |  |
| Propylene glycol | 21.18 |
| Tetrasodium EDTA | 0.22 |
| Westchlor A2Z8106 | 40.75 |
| Abil B8851 | 0.28 |
| Subtotal | 62.43 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 125–130° C. while stirring at the minimum speed of ~50 rpm with a Caframo Model RZR1 electric mixer equipped with a Jiffy Model HS150 2.62 inch diameter mixer. The Natrosol® Plus 430 material was added at about 75–80° C., and the mixture was continued heating to about 120–130° C. The mixer speed was increased to 150–200 rpm and the Millithix material was added at about 120° C. and mixed for about 40 minutes to dissolve.

Phase 2.

Approximately one-third of the total propylene glycol was charged to about 600 ml beaker and immersed in a circulating water bath. The propylene glycol was heated to about 80–85° C. while stirring at minimum speed (~50 rpm) with a Caframo Model RZR1 electric mixer equipped with a single two-inch diameter propellor blade. The EDTA was added at 80–85° C. and mixed well to disperse. The mixer speed was increased to 150–200 rpm and the Westchlor material was added at about 80–85° C. while mixing and mixed. The Abil material was then added at about 80–85° C. while mixing and mixed for five minutes.

Combined Phases:

Phase 2, at about 80–85° C., was added to Phase 1 at about 130° C. while mixing and mixed for about 15 minutes at reduced speed to avoid air entrainment. The combined solution was re-heated to about 120–125° C. while mixing, then poured into four four-ounce jars and four 17-ml vials for testing and allowed to cool to room temperature.

EXAMPLE 6

Formulation:

|  | Percent |
| --- | --- |
| Phase 1: | |
| Propylene glycol | 35.50 |
| Natrosol ® Plus 430 | 0.55 |
| Millithix 925 | 1.10 |
| Crodacol C-95 | 1.10 |
| Subtotal | 38.26 |
| Phase 2: | |
| Propylene glycol | 20.94 |
| Tetrasodium EDTA | 0.22 |
| Westchlor A2Z8106 | 40.30 |
| Abil B8851 | 0.28 |
| Subtotal | 61.74 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 125–130° C. while stirring at the minimum speed of ~50 rpm with a Caframo Model RZR1 electric mixer equipped with a Jiffy Model HS150 2.62 inch diameter mixer. The Natrosol® Plus 430 material was added at about105–110° C., and the mixture was continued heating to about 120–130° C. The mixer speed was increased to 150–200 rpm and the Millithix material was added at about 120° C. and mixed for about 40 minutes to dissolve. The Crodacol C-95 was then added at about 132° C. and mixed for about 15 minutes.

Phase 2.

Approximately one-third of the total propylene glycol was charged to a 600 ml beaker and immersed in a circulating water bath. The propylene glycol was heated in beaker to about 80–85° C. while stirring at minimum speed (~50 rpm) with a Caframo Model RZR1 electric mixer equipped with a single two-inch diameter propellor blade. The EDTA was added at 75–80° C. and mixed well to disperse. The mixer speed was increased to 150–200 rpm and the Westchlor material was added at about 80–85° C. while mixing and mixed until. The Abil material was then added at about 80–85° C. while mixing and mixed for about five minutes.

Combined Phases:

Phase 2, at about 82° C., was added to Phase 1 at about 131° C. while mixing and mixed for about 15 minutes at reduced speed to avoid air entrainment. The combined solution was re-heated to about 120–125° C. while mixing, then poured into four four-ounce jars and four 17-ml vials for testing and allowed to cool to room temperature.

EXAMPLE 7

Formulation:

|  | Percent |
| --- | --- |
| Phase 1: | |
| Propylene glycol | 35.31 |
| Natrosol ® Plus 430 | 0.55 |
| Millithix 925 | 1.10 |
| Crodacol C-95 | 1.10 |
| Subtotal | 38.05 |
| Phase 2: | |
| Propylene glycol | 20.83 |
| Tetrasodium EDTA | 0.22 |
| Westchlor A2Z8106 | 40.08 |
| Abil B8851 | 0.27 |
| Subtotal | 61.41 |
| Phase 3: | |
| Fragrance SL91-2007 | 0.55 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 125–130° C. while stirring at the minimum speed of ~50 rpm with a Caframo Model RZR1 electric mixer equipped with a Jiffy Model HS150 2.62 inch diameter mixer. The Natrosole® Plus 430 material was added at about 85–90° C., and the mixture was continued heating to about 120–130° C. The mixer speed was increased to about 150–200 rpm and the Millithix material was added at about 120° C. and mixed for about 25 minutes to dissolve. The Crodacol C-95 material was then added at about 130° C. and mixed for about 15 minutes.

Phase 2.

Approximately one-third of the total propylene glycol was charged to about 600 ml beaker and immersed in a circulating water bath. The propylene glycol was heated in a beaker to about 80–85° C. while stirring at minimum speed (~50 rpm) with a Caframo Model RZR1 electric mixer equipped with a single two-inch diameter propellor blade. The EDTA was added at about 55–60° C. and mixed well to disperse. The mixer speed was increased to about 150–200 rpm and the Westchlor material was added at about 80–85° C. while mixing and mixed. The Abil material was then added at about 80–85° C. while mixing and mixed for about ten minutes.

Combined Phases:

Phase 2, at about 82° C., was added to Phase 1 at about 131° C. while mixing and mixed for about 10 minutes at reduced speed to avoid air entrainment. The fragrance was injected into the combined solution with a syringe through the saran cover to minimize loss. The batch at about 120–125° C. was then poured into four four-ounce jars and four 17-ml vials for testing and allowed to cool to room temperature.

Source and Description of Products Used

EXAMPLE 7

| Source and Description of Products Used | | |
| --- | --- | --- |
| Crodacol C-95 | Cetyl alcohol | Croda, Inc. Parsippany, NJ |
| SL91-2007 | Fragrance, Masculine IV | PFW, Inc. Middletown, NY |

EXAMPLE 8

Formulation:

| | Percent |
| --- | --- |
| Phase 1: | |
| Propylene glycol | 35.54 |
| HMHAC1 | 0.99 |
| Millithix 925 | 1.65 |
| Subtotal | 38.19 |
| Phase 2: | |
| Propylene glycol | 20.97 |
| Tetrasodium EDTA | 0.22 |
| Westchlor A2Z8106 | 40.35 |
| Abil B8851 | 0.28 |
| Subtotal | 61.81 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated while stirring at the minimum speed of ~50 rpm with a Caframo Model RZR1 electric mixer equipped with a Jiffy Model HS150 2.62 inch diameter mixer. The HMHAC1 material was added at about 75–80° C. while mixing and the mixture was continued to heat to about 105–110° C. The mixer speed was increased to about 150–200 rpm and the Millithix material was added and mixed for about 15 minutes until dissolved.

Phase 2.

Approximately one-third of the total propylene glycol was charged to a 600 ml beaker and immersed in a circulating water bath. The propylene glycol was heated in a beaker to about 80–85° while stirring at minimum speed (~50 rpm) with a Caframo Model RZR1 electric mixer equipped with a single two-inch diameter propellor blade. The EDTA was added at about 45–50° C. and mixed well to disperse. The mixer speed was increased to about 150–200 rpm and the Westchlor material was added at about 55–60° C. while mixing and mixed for five minutes until clear and homogeneous. The Abil material then was added at about 75–80° C. while mixing and mixed for five minutes.

Combined Phases:

When the Millithix material was all dissolved, Phase 2, at about 77° C., was added to Phase 1 at about 125° C. while mixing and mixed for five minutes at reduced speed to avoid air entrainment. The combined solution was re-heated to about 120° C., then poured into four four-ounce jars and four 17-ml vials for testing and allowed to cool to room temperature.

EXAMPLE 9

Formulation:

| | Percent |
| --- | --- |
| Phase 1: | |
| Propylene glycol | 35.50 |
| Polysurf 67 | 1.10 |
| Millithix 925 | 1.65 |
| Subtotal | 38.26 |
| Phase 2: | |
| Propylene glycol | 20.94 |
| Tetrasodium EDTA | 0.22 |
| Westchlor A2Z8106 | 40.30 |
| Abil B8851 | 0.28 |
| Subtotal | 61.74 |
| Total | 100.00 |

Procedure:

Phase 1.

Approximately two-thirds of the total propylene glycol was charged to a one-liter beaker and immersed in a circulating oil bath. The beaker was kept covered with saran wrap throughout the preparation to minimize loss of volatiles. The propylene glycol was heated to about 125–130° C. while stirring at the minimum speed of ~50 rpm with a Caframo Model RZR1 electric mixer equipped with a Jiffy Model HS150 2.62 inch diameter mixer. The Polysurf 67 material was added at about 90–95° C. while mixing for about 15 minutes, and the mixture was continued heating to about 120–130° C. The mixer speed was increased to about 150–200 rpm and the Millithix material was added at about 120° C. and mixed for about 40 minutes to dissolve.

Phase 2.

Approximately one-third of the total propylene glycol was charged to about 600 ml beaker and immersed in a circulating water bath. The propylene glycol was heated in a beaker to about 80–85° C. while stirring at minimum speed (~50 rpm) with a Caframo Model RZR1 electric mixer equipped with a single two-inch diameter propellor blade. The EDTA was added at about 70–75° C. and mixed well to disperse. The mixer speed was increased to about 150–200 rpm and the Westchlor material was added while mixing and mixed. The Abil material was then added at about 80–85° C. while mixing and mixed for about five minutes.

Combined Phases:

Phase 2, at about 80–85° C., was added to Phase 1 at about 130° C. while mixing and mixed for about five minutes at reduced speed to avoid air entrainment. The combined solution was re-heated to about 125–130° C. while mixing an additional about 20 minutes to dissolve a few remaining particles, then poured into four four-ounce jars and four 17-ml vials for testing and allowed to cool to room temperature.

EXAMPLE 10

Formulation:

| | Percent |
| --- | --- |
| Propylene glycol | 56.45 |
| Polysurf 67 | 1.10 |
| Millithix 925 | 1.65 |
| Tetrasodium EDTA | 0.22 |

EXAMPLE 10-continued

Formulation:

| | Percent |
|---|---|
| Westchlor A2Z8106 | 40.30 |
| Abil B8851 | 0.28 |
| Subtotal | 100.00 |

Procedure:

Phase 1.

The propylene glycol was charged to a one-liter beaker and immersed in a circulating oil bath. The beaker was kept covered with saran wrap throughout the preparation to minimize loss of volatiles. The propylene glycol was heated to about 120–130° C. while stirring at the minimum speed of ~50 rpm with a Caframo Model RZR1 electric mixer equipped with a Jiffy Model HS150 2.62 inch diameter mixer. The Polysurf 67 material was added at about 60–65° C., and the mixture was continued heating to about 120–130° C. The mixer speed was increased to about 150–200 rpm and the Millithix material was added at about 107° C. and mixed for about 60 minutes at about 120–130° C. to dissolve. The EDTA, Westchlor material were added in order at about 130° C. and mixed five minutes after each addition. The Abil material was added at about 104° C. and mixed at about 15 minutes. The combined solution was re-heated to about 120–125° C. while mixing, then poured into four four-ounce jars and four 17-ml vials for testing and allowed to cool to room temperature.

What is claimed:

1. A solid stick underarm product composition comprising (a) a liquid vehicle, (b) an antiperspirant salt, (c) dibenzylidene alditol gelling agent, and (d) a co-gelling agent of a hydrophobically modified water soluble polysaccharide polymer where the hydrophobic moiety is selected from the class consisting of $C_8$–$C_{24}$ alkyl, aryl alkyl, alkyl aryl groups and mixtures thereof, wherein the hydrophobic moiety is present in an amount up to the amount which renders said polysaccharide less than 1% by weight soluble in water.

2. The solid stick underarm product composition of claim 1, wherein the liquid vehicle is a polyhydric alcohol having from 3 to 6 carbon atoms and 2 to 6 hydroxyl group.

3. The solid stick underarm product composition of claim 2, wherein the liquid vehicle is selected from the group consisting of diethylene glycols, triethylene glycols, 1,2-propylene glycol, 1,3-propylene glycol, dipropyleneglycol, tripropylene glycol, 2-methyl-1,3-propendiol, buetlene glycol, sorbitol, 2,4-dihydroxy-2-methylpentane, and the like, and mixtures thereof.

4. The solid stick underarm product composition of claim 1 wherein the liquid vehicle contains a member selected from the group consisting of ethanol, isopropanol, and ethylene glycol.

5. The solid stick underarm product composition of claim 2, wherein the liquid vehicle is propylene glycol.

6. The solid stick underarm product composition of claim 1, wherein the antiperspirant salt is selected from the group consisting of a salt of aluminum, zirconium, zinc and mixtures thereof.

7. The solid stick underarm product composition of claim 6, wherein the antiperspirant salt is selected from the group consisting of aluminum halides, aluminum hydroxy halides, and mixtures.

8. The solid stick underarm product composition of claim 7, wherein the antiperspirant salt is a complex thereof with zirconyl oxyhalides or zirconyl hydroxyhalides.

9. The solid stick underarm product composition of claim 8, wherein the antiperspirant salt is aluminum zirconium pentacholorhydratex-gly dissolved in propylene glycol.

10. The solid stick underarm product composition of claim 1, wherein the dibenzylidene alditol gelling agent is selected from the group consisting of dibenzylidene sorbitol (DBS), dibenzylidene monosorbitol acetal (DBMSA), dibenzylidene xylitol, and dibenzylidene ribitol.

11. The solid stick underarm product composition of claim 10, wherein the dibenzylidiene alditol gelling agent is dibenzylidiene sorbitol.

12. The solid stick underarm product composition of claim 1, wherein the underarm composition has by weight percent of from about 70% to about 95% liquid vehicle, about 0.5% to about 20% antiperspirant salt, about 0.3% to about 5.0% dibenzylidene alditol, and about 0.1 to about 3.0% hydrophobically modified water soluble polysaccharide.

13. The solid stick underarm product composition of claim 1, wherein the hydrophobically modified water soluble polysaccharide has a backbone that is selected from the group consisting of cellulose ethers, guar and guar derivatives, and starch and starch derivatives.

14. The solid stick underarm product composition of claim 13, wherein the polysaccharide backbone is a cellulose ether.

15. The solid stick underarm product composition of claim 14, wherein polysaccharide backbone is selected from the group consisting of hydroxyethylcellulose (HEC), hydroxypropylcellulose (HPC), methylcellulose (MC), hydroxypropylmethylcellulose (HPMC), ethylhydroxyethylcellulose (EHEC), and methylhydroxyethylcellulose (MHEC, and mixtures thereof.

16. The solid stick underarm product composition of claim 15, wherein the polysaccharide backbone is HEC.

17. The solid stick underarm product composition of claim 15, wherein the polysaccharide backbone is HPC.

18. The solid stick underarm product composition of claim 13, wherein the guar derivative is hydroxyethyl guar or hydroxypropyl guar.

19. The solid stick underarm product composition of claim 13, wherein the starch derivative is hydroxyethyl starch or hydroxypropyl starch.

20. The solid stick underarm product composition of claim 13, wherein the hydrophobic moiety is attached to the backbone via ether, ester, or urethane linkage.

21. The solid stick underarm product composition of claim 20, wherein the linkage is ether.

22. The solid stick underarm product composition of claim 1, wherein the hydrophobic moiety has an upper limit of 22 carbons.

23. The solid stick underarm product composition of claim 1, wherein the hydrophobic moiety has an upper limit of 18 carbons.

24. The solid stick underarm product composition of claim 1, wherein the hydrophobic moiety has a lower limit of 12 carbons.

25. The solid stick underarm product composition of claim 1, wherein the hydrophobic moiety is cetyl.

26. The solid stick underarm product composition of claim 1, wherein the hydrophobic moiety is octyl.

27. The solid stick underarm product composition of claim 1, wherein the composition further comprises at least one member selected from the group consisting of chelating agent, emollient, stabilizer, fragrance, color, filler, humectant, UV absorbers, sunscreen, antioxidant, and bactericide.

28. The solid stick underarm product composition of claim 27, wherein the emollient is at least one member selected from the group consisting of fatty acid esters, diesters of adipic, phthalic, and sebasic acids, propylene glycol diesters of short chain fatty acids, nonvolatile silicone oils, volatile silicone oils, silicone elastomers, $C_{12}$–$C_{15}$ alkyl benzoate, fatty alcohols, alkyl ether derivatives of polyethylene glycols, polypropylene glycols, and mixtures thereof.

29. The solid stick underarm product composition of claim 27, wherein the chelating agent is selected from salts of ethylenediamine tetraacetic acid (EDTA).

30. The solid stick underarm product composition of claim 27, wherein the stabilizer is selected from the group consisting of sodium or potassium hydroxide, zinc acetate, zinc oxide, zinc carbonate, di or tri-ethanolamine, sodium benzoate, sodium octanoate, urea, and disodium succinate.

31. The solid stick underarm product composition of claim 1, wherein the composition is a clear or hazy solid stick product.

\* \* \* \* \*